US005818947A

United States Patent [19]

Cattafesta, III et al.

[11] Patent Number: 5,818,947

[45] Date of Patent: Oct. 6, 1998

[54] REDUCING FLOW-INDUCED RESONANCE IN A CAVITY

[75] Inventors: Louis N. Cattafesta, III; Richard W. Wlezien; Chin C. Won, all of Yorktown; Sanjay Garg, Wiliamsburg, all of Va.

[73] Assignee: High Technology Corporation, Hampton, Va.

[21] Appl. No.: 751,179

[22] Filed: Nov. 15, 1996

[51] Int. Cl.$^{6}$ .................................................. A61F 11/06

[52] U.S. Cl. ........................................ 381/71.7; 244/130

[58] Field of Search .............................. 381/71, 94, 71.1, 381/71.2, 71.5, 71.7, 71.8, 71.14, 94.1; 181/206; 244/130, 198, 199, 204

[56] References Cited

U.S. PATENT DOCUMENTS 5,493,615 2/1996 Burke et al. .............................. 381/71

5,606,214 2/1997 Corsaro .................................. 310/329

*Primary Examiner*—Vivian Chang

*Attorney, Agent, or Firm*—Peter J. Van Bergen

[57] ABSTRACT

A method and system are provided for reducing flow-induced resonance in a structure's cavity. A time-varying disturbance is introduced into the flow along a leading edge of the cavity. The time-varying disturbance can be periodic and can have the same or different frequency of the natural resonant frequency of the cavity. In one embodiment of the system, flaps are mounted flush with the surface of the structure along the cavity's leading edge. A piezoelectric actuator is coupled to each flap and causes a portion of each flap to oscillate into and out of the flow in accordance with the time-varying function. Resonance reduction can be achieved with both open-loop and closed-loop configurations of the system.

7 Claims, 3 Drawing Sheets

REDUCING FLOW-INDUCED RESONANCE IN A CAVITY

STATEMENT OF GOVERNMENT INTEREST

This invention was made with Government support under contract NAS2-13968 awarded by NASA. The Government has certain rights in this invention.

FIELD OF THE INVENTION

The invention relates generally to flow-induced cavity resonance, and more particularly to a method and system for reducing resonance in a structure's cavity caused by a flow passing over the surface of the structure and the cavity.

BACKGROUND OF THE INVENTION

The control of the resonant interaction between a free shear layer and a cavity is of direct relevance to many wind tunnel testing and aircraft applications. Acoustic levels in zones of local flow separation such as gaps, cavities, and junctures can generate pure tone acoustic components having large amplitudes which, at a minimum, contaminate acoustic field measurements and which, in the extreme, lead to fatigue of components and systems. Such cavities exist in landing gear bays, weapon delivery systems, optics bays, at junctions between wind tunnel model components, and in a variety of instrument installation configurations. Cavity noise is a major reliability and maintainability issue in several aircraft programs, and can be a dominant factor in determining the success of programs with instrumentation in cavities. Thus, the control of internal cavity dynamic loads is an issue of critical importance.

The complex nature of cavity flows is illustrated in FIG. 1. A thick (usually turbulent) boundary layer represented by arrow profile 10 separates at the upstream or leading edge 102 of a cavity 101 formed in a portion of a structure 100 which is shown in cross-section. Local conditions such as the shape of leading edge 102 control the actual separation location. A leading edge 102 that is sharp fixes the separation location but also enhances shear-layer receptivity to acoustic disturbances. The unsteady characteristics of the resulting free shear layer (represented in FIG. 1 by the area between lines 11 and 12) over cavity 101 are determined by the mean profile and turbulence characteristics of incoming boundary layer 10 as well as the disturbances imposed on the shear layer through the receptivity process. The shear layer between lines 11 and 12 develops based on the separating shear layer conditions and the instability characteristics of the mean shear layer profile. Velocity profile shaping can be used with some success to move the amplification band away from those frequencies tuned to cavity resonance.

Leading edge 102 is the significant location for acoustic receptivity which is defined as the process by which long wavelength acoustic disturbances couple with the shorter wavelength disturbances in the separating free shear layer. When leading edge 102 is sharp, the shear layer is highly susceptible to the unsteady pressure gradients imposed by the interaction between the incident acoustic field and leading edge 102. If leading edge 102 is blunt, it produces significantly lower receptivity to externally imposed acoustic fields.

The shear layer subsequently reattaches to the surface of structure 100 at the aft end of cavity 100. Trailing edge 103 serves as the primary acoustic source. In cases where reattachment is delayed until past trailing edge 103 of cavity 100, the reattachment is more benign and the acoustic levels are reduced in amplitude. Rounded or perforated trailing edges have been used to modify the reattachment zone and decrease the amplitude of the acoustic disturbance field.

The sound produced when the shear layer reattaches to the aft cavity wall of structure 100 provides the primary acoustic source that drives the cavity acoustics. The geometric shape of cavity 101 determines which specific acoustic modes dominate. Furthermore, a cavity having regular internal dimensions will produce the greatest resonant amplitudes. Since the shear layer provides a wide range of source frequencies, there exists the possibility that natural cavity resonances will be stimulated. Irregular cavity dimensions will reduce the peak acoustic amplitudes, but in turn will ensure that resonance conditions exist over a wide range of frequencies and operating conditions. Thus, passive geometric modifications to the cavity or its surrounding environment will not necessarily lead to a solution of the resonance problem over a wide range of frequencies and operating conditions.

Another source of resonance in cavity 101 is the feedback of energy (represented in FIG. 1 by the curved arrow referenced by numeral 13) to leading edge 102 where the initial separation occurs. The amplitude and frequency content of feedback 13 ultimately controls the shear layer disturbance. Some reduction of feedback 13 can be achieved through the use of sound-absorbing cavity liners. However, while reducing resonance amplitude and generation of tones, such liners are typically not effective at low acoustic frequencies because the thickness of the liners becomes large compared to the cavity dimensions. Therefore, additional noise reduction mechanisms are generally used in conjunction with such liners.

Acoustic amplitude reduction can also be achieved by introducing cancellation noise from one or more acoustic sources. This approach has successfully been employed in the prior art for reduction of low-frequency components of noise emitted from exhaust systems, for ambient noise reduction in headsets, and for localized noise reduction in aircraft interiors. When the acoustic sources are configured with the appropriate phase, amplitude, and frequency content, acoustic levels can be minimized within certain constraints. For example, in duct propagation where plane waves are the dominant component, the plane waves can effectively be canceled with a limited number of sources. However, in more complex three-dimensional environments such as cavities, it is only possible to minimize the noise at a limited number of locations. In essence, the number of active sources controls the number of degrees of freedom available for active cancellation. Thus, active cancellation is not a practical option for lowering acoustic levels within an entire cavity. In addition, the large sound levels encountered in the cavity require impractical power inputs for effective sound cancellation.

SUMMARY OF THE INVENTION

Accordingly, it is an object of the present invention to provide a method and system for reducing flow-induced resonance in a cavity.

Another object of the present invention is to provide a method and system for reducing flow-induced resonance in a cavity over a range of flow conditions.

Still another object of the present invention to provide a method and system that dynamically adjusts to changing flow conditions in order to reduce flow-induced resonance in a cavity.

Other objects and advantages of the present invention will become more obvious hereinafter in the specification and drawings.

In accordance with the present invention, a method and system are provided for reducing resonance in a structure's cavity that is induced by a flow passing over the cavity. The method is accomplished by introducing a time-varying disturbance into the flow along the leading edge of the cavity. The time-varying disturbance can be periodic and can have the same or different frequency of the natural resonant frequency of the cavity. In one embodiment of the system, one or more flaps are mounted flush with the surface of the structure along the leading edge of the cavity. The leading edge is defined with respect to the direction of the flow. An actuator is coupled to each flap and causes a portion of each flap to oscillate into and out of the flow in accordance with the time-varying function. Resonance reduction can be achieved with both open-loop and closed-loop configurations of the system.

DETAILED DESCRIPTION OF THE INVENTION

Figure 1:
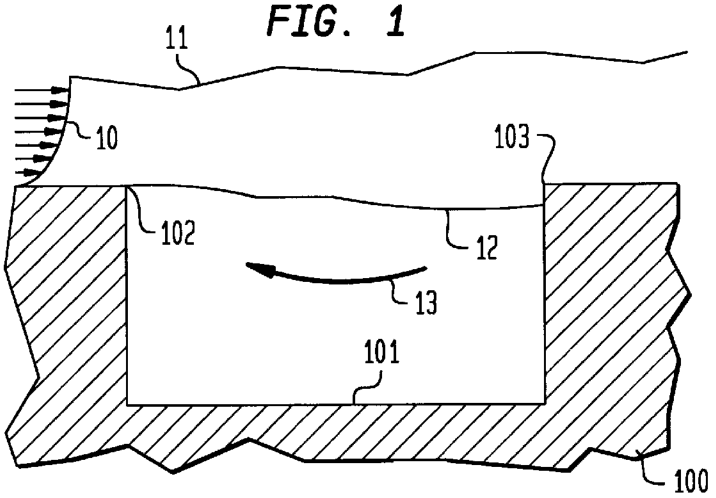
FIG. 1 is a schematic view illustrating flow separation over a cavity as a source of acoustic resonance in the cavity.
Figure 2:
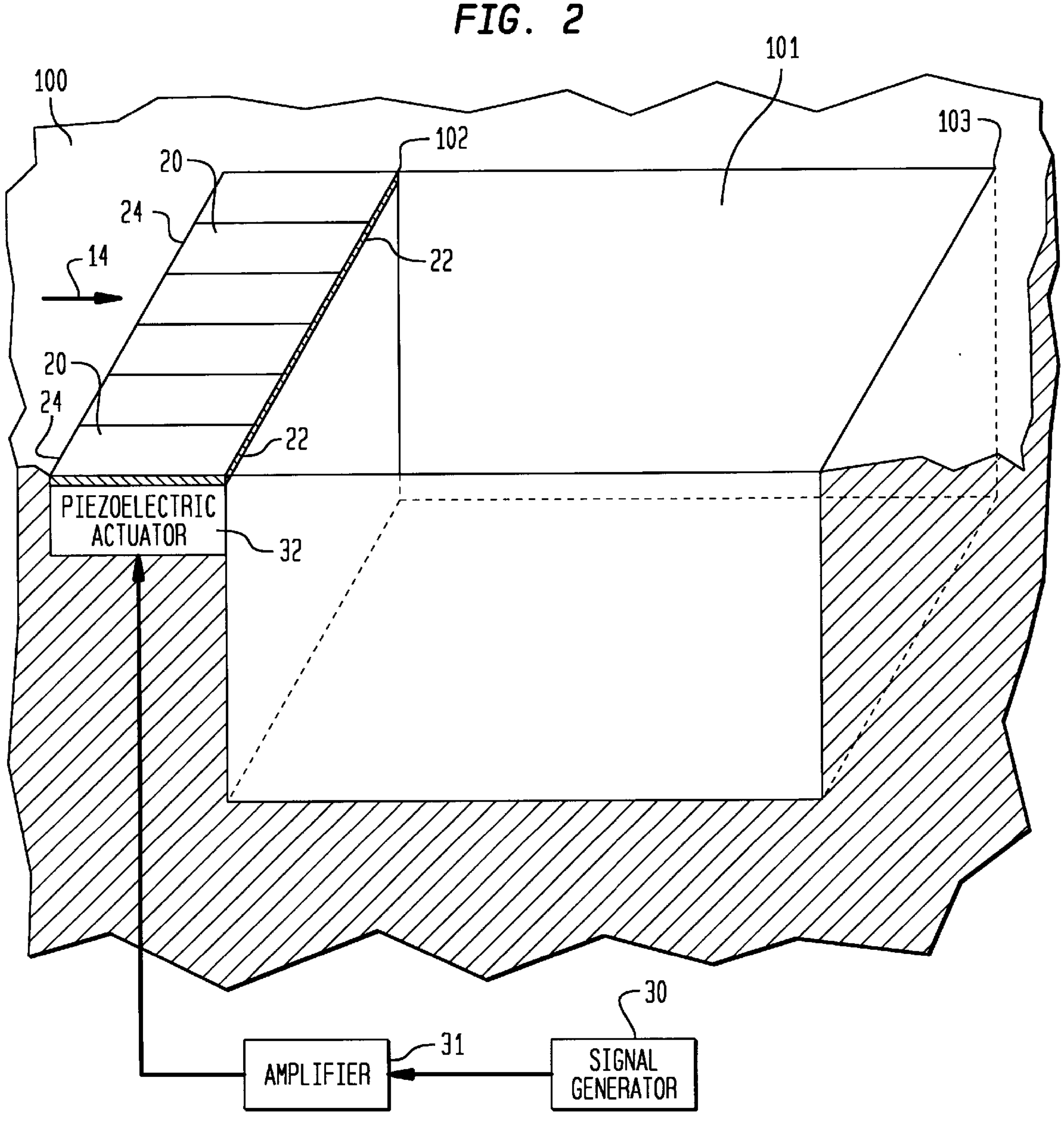
FIG. 2 is a schematic view of an open-loop system used to reduce cavity resonance in accordance with the present invention.

Referring again to the drawings, and more particularly to FIG. 2, a schematic view is shown of a cavity 101 in a structure 100 equipped with an open-loop cavity resonance reduction system of the present invention. The shape and relative size of cavity 101 are for illustrative purposes only as the present invention will work with any shape or size cavity. Flow over structure 100 and cavity 101 is represented by the arrow referenced by numeral 14. The leading and trailing edges of cavity 101 are defined in terms of flow 14. More specifically, leading edge 102 is the first edge of cavity 101 encountered by flow 14 and trailing edge 103 is the last edge of cavity 101 encountered by flow 14.

In the present invention, one or more flaps (e.g., a plurality are shown in FIG. 2) 20 are mounted in or on structure 100 such that they are flush with the surface of structure 100 in their "at rest" position. Each of flaps 20 is aligned along leading edge 102 with its free or outboard end 22 thereof terminating at leading edge 102 and with its fixed end 24 located upstream of free end 22.

In the open-loop configuration, free end 22 of each flap 20 is oscillated into and out of flow 14. Such oscillation is controlled in accordance with a time-varying function supplied by a signal generator 30 and amplified by an amplifier 31. The output from amplifier 31 is coupled to a piezoelectric actuator 32 associated with a corresponding one of flaps 20. Each flap 20 and its piezoelectric actuator 32 form an "active" flap.

Figure 3:
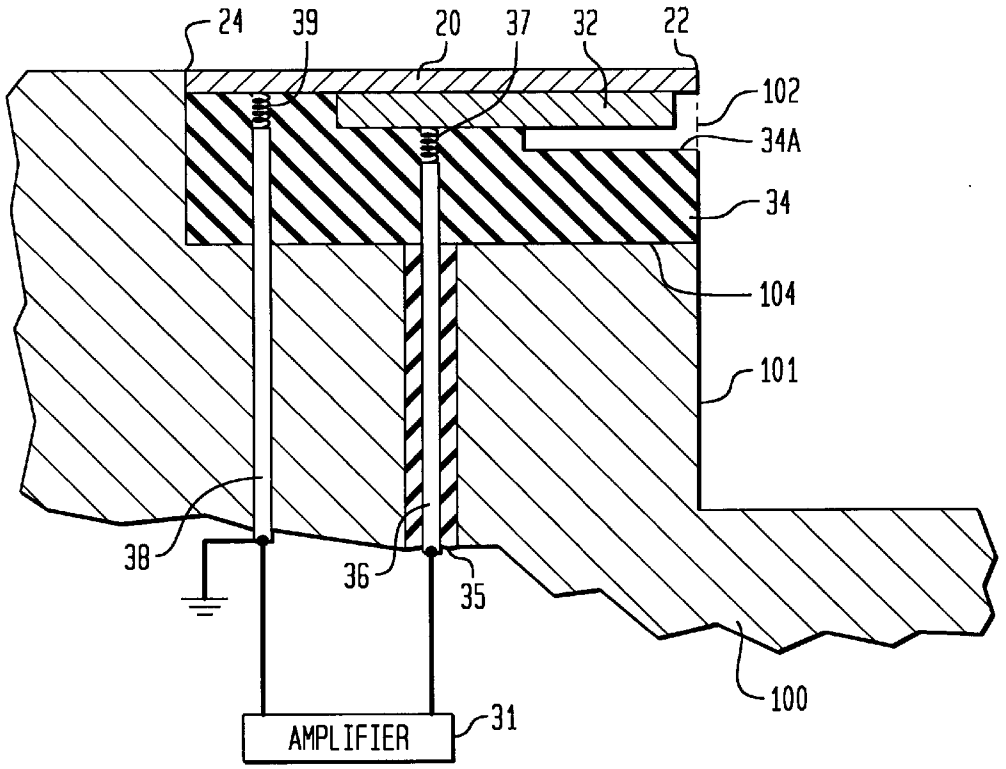
FIG. 3 is a cross-sectional view of a flap and actuator construction used in an embodiment of the present invention.

One construction of flap 20 and actuator 32 mounted in structure 100 at leading edge 102 is shown in FIG. 3. In order to allow flap 20 to lie flush with the surface of structure 100 in its "at rest" or inactivated position, an indentation or cutout 104 is formed just upstream of leading edge 102. In this embodiment, each "active" flap includes flap 20 made from an electrically conductive material, e.g., steel, and actuator 32 made from a layer of piezoelectric material, e.g., piezoceramic, bonded to flap 20 over an appropriate area thereof. Since structure 100 is typically metal, a layer 34 of electrically insulating material, e.g., plexiglas, is provided between and bonded to piezoelectric actuator 32 and structure 100 by bonding agents (not shown) well known in the art. Insulating material layer 34 has a notch 34A formed therein and extending to leading edge 102 where piezoelectric actuator 32 is not bonded to insulating layer 34. In this way, free end 22 can flex both towards and away from structure 100 when piezoelectric actuator 32 is appropriately driven by signal generator 30/amplifier 31.

Electrical coupling of amplifier 31 to flap 20 and piezoelectric actuator 32 is as follows. One electrical connection between amplifier 31 and piezoelectric actuator 32 is made via an electrically conductive post 36 passing through structure 100 and insulating layer 34. If structure 100 is metal, post 36 must be electrically insulated from structure 100 by insulating sleeve 35. To complete the electrical circuit, a ground electrical connection from amplifier 31 is made to flap 20 via electrically conductive post 38 passing through structure 100 and insulating layer 34. If structure 100 is metal, post 38 can contact structure 100 which then serves as ground potential as shown in FIG. 3.

The bonds between flap 20, piezoelectric actuator 32 and insulating layer 34, will undergo cyclic loading as flap 20 and piezoelectric actuator 32 oscillate in accordance with a time-varying function originating at signal generator 30. To insure the integrity of these bonds and thereby provide a robust active flap design, the electrical connection of posts 36 and 38 should be mechanically resilient. One way of accomplishing this is shown in FIG. 3 where posts 36 and 38 incorporate electrically conductive springs 37 and 39, respectively, at the point of contact with piezoelectric actuator 32 and flap 20, respectively.

Figure 4:
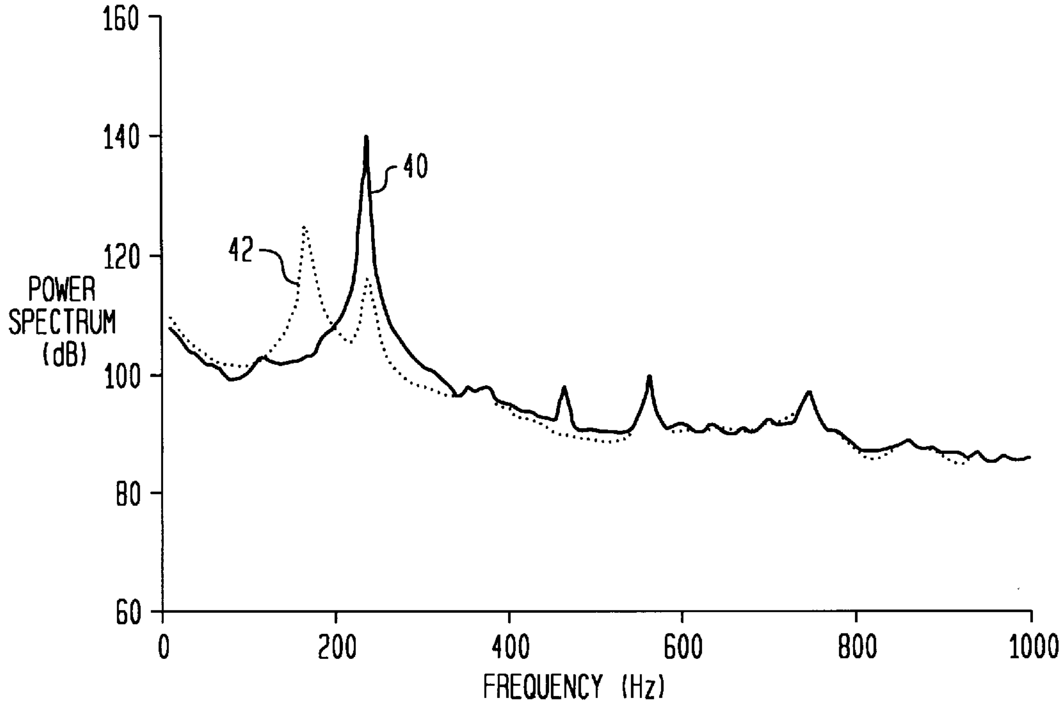
FIG. 4 is a graph comparing the sound power spectrum versus frequency for a cavity without the present invention and with the open-loop configuration of the present invention.

Before describing the operation of the open-loop configuration shown in FIG. 2, the operating principles of the present invention will be explained. Flow disturbances (such as those in the free shear layer formed during separation at the cavity leading edge) draw their energy from the energy in the flow itself. Cavities have natural resonant frequencies at which the largest sound levels occur. The natural resonant frequencies of a cavity are generally a function of the cavity dimensions, and the speed and Mach number of the flow thereover. These frequencies can be determined by measuring sound levels in the cavity using sensors (e.g., microphones, velocity sensors, etc.) placed in the cavity. Generally, there is one dominant frequency of oscillation at which a large fraction of the sound is generated. Since the energy of any flow is finite, the present invention operates to draw energy from the flow so that less energy is available at, for example, the dominant natural resonant frequency of the cavity. This is best explained with the aid of FIG. 4 where curve 40 represents the sound power spectrum of cavity resonance versus frequency for a cavity without the resonance reduction of the present invention. Curve 40 was generated for a cavity having a length-to-depth ratio of 0.5 that experienced a flow of air thereover having a free stream velocity of 40 meters/second and a Mach number of 0.13.

From curve 40, it is clear that several natural resonant frequencies are present and the peak cavity resonance occurs at approximately 230 Hz where sound pressure levels reached approximately 140 dB. Note that the remaining resonance peaks at other frequencies do not exceed 110 dB. Accordingly, a great reduction in overall cavity resonance can be achieved by reducing the contribution of, for example, the sound generated at the dominant natural resonant frequency.

The present invention achieves cavity resonance reduction by introducing a disturbance into the flow (i.e., free end 22 of flap 20 moving into and out of flow 14) at the leading edge of the cavity. The introduced disturbance extracts energy from the finite energy of the flow thereby making less energy available for the disturbance in the shear layer at, for example, the dominant natural resonant frequency of the cavity. The introduced disturbance should be based on a time-varying function and is typically a periodic function having a fundamental frequency that is different than, for example, the dominant natural resonant frequency. (Note that the present invention could also be practiced by introducing a disturbance in accordance with a periodic function at a natural resonant frequency of the cavity as long as the introduced disturbance was the same magnitude and 180° out-of-phase with respect to the resonant disturbance in the cavity at the selected natural resonant frequency. This approach of noise cancellation is effective only when the signals are "deterministic", i.e., show no random variation in amplitude and phase with respect to time.)

Referring again to FIG. 3, the power spectrum represented by dashed-line curve 42 shows the benefits of an open-loop resonance reduction system of the present invention. By way of example, curve 42 represents the sound pressure levels measured when flaps 20 were driven by a 170 Hz sine wave in the same flow conditions that were used during the measurement of curve 40. Curve 42 represents a spectrum that has its largest peak at 170 Hz. However, this peak is approximately 15 dB less than the 140 dB occurring at the dominant natural resonant frequency of 230 Hz for curve 40. In addition, the peak at this dominant natural resonant frequency of the cavity is reduced by approximately 25 dB. (Note that 20 dB is equivalent to a factor of ten reduction in sound.) The overall sound level (found by integrating over the entire frequency spectrum) is reduced by approximately 12 dB. Similar but quantitatively different results can be obtained for different amplitudes and frequencies of flap excitation.

In the illustrated example, all flaps were driven with the same signal so that all flaps 20 oscillated in unison, i.e., driven in phase. Thus, the same result might have been achieved using a single flap. However, while this may be possible for cavities of small width (e.g., less than 2 inches), there are a number of practical benefits to using a plurality of individual adjacent flaps or a segmented flap. For example, one large flap may not be able to respond well to the optimal time-varied function. This is because frequency response degrades as the "flap" starts to react more as a "plate" than a "beam". Also, the use of a plurality of flaps, each of which can be independently actuated, allows for the application of unique actuation functions (in terms of amplitude, frequency and/or phase) for each flap. In addition, should one actuator/flap combination fail, the remaining actuators/flaps can still achieve some measure of cavity resonance reduction.

Figure 5:
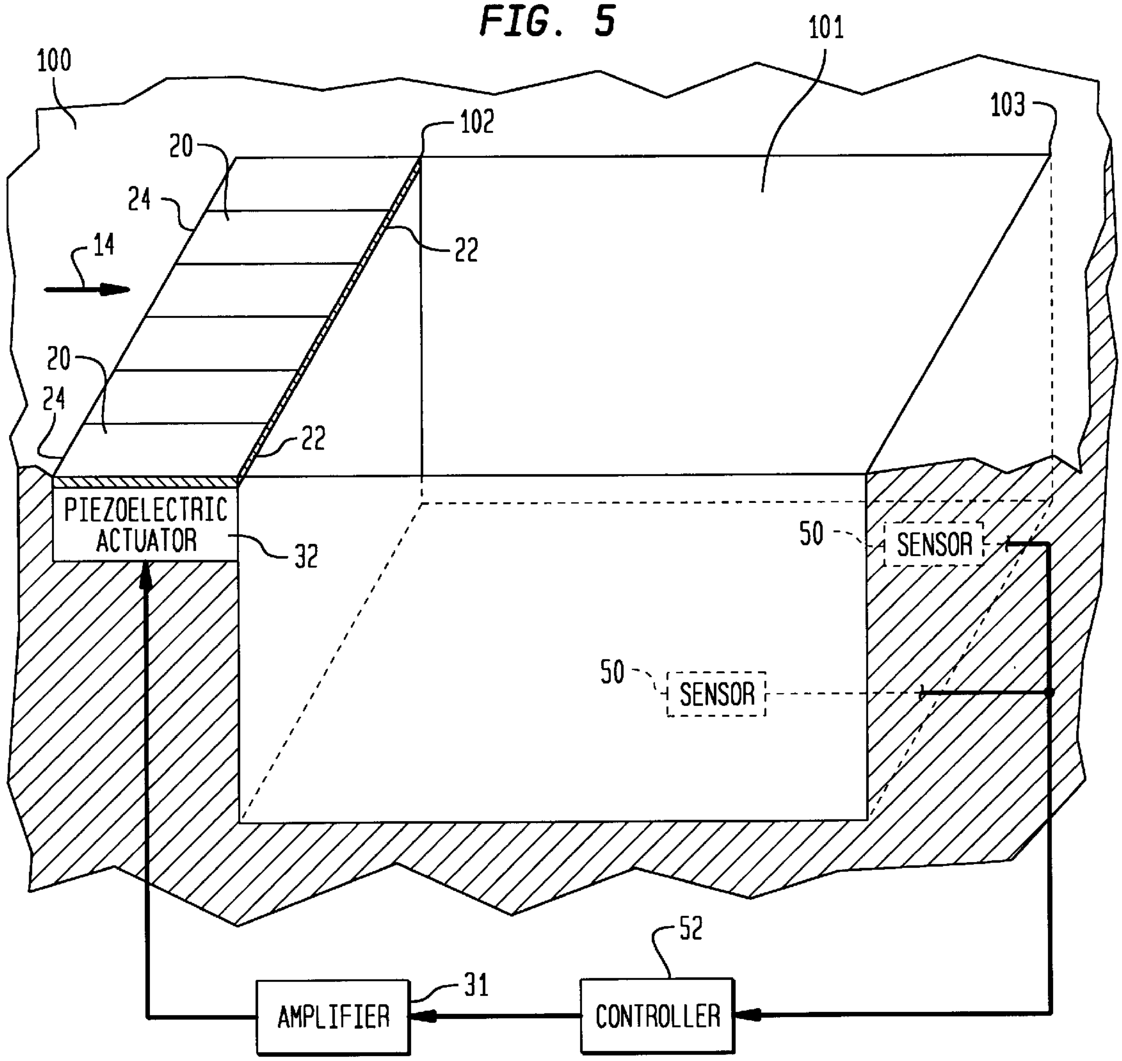
FIG. 5 is a schematic view of a closed-loop system used to reduce cavity resonance according to the present invention.
Figure 6:
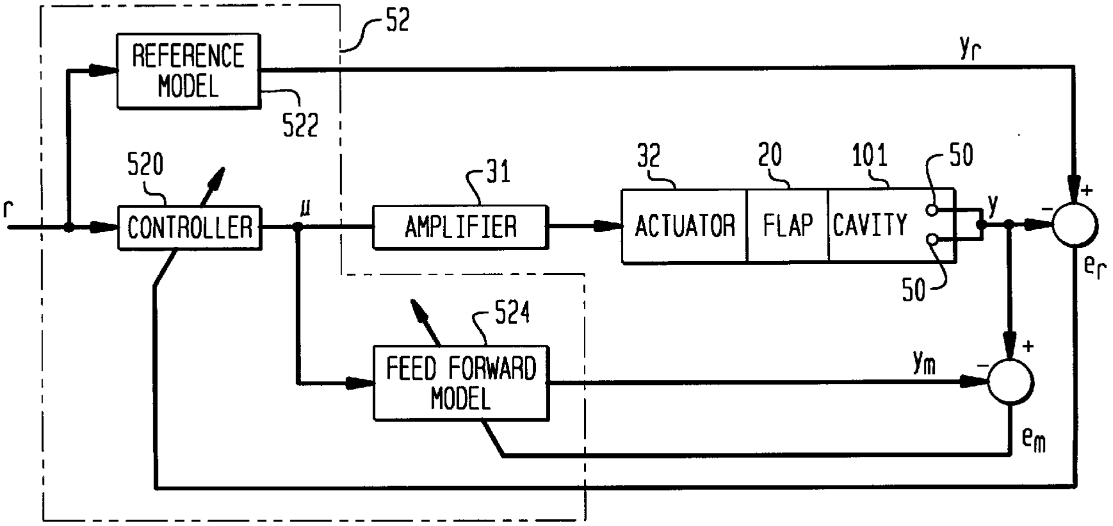
FIG. 6 is a schematic view of an example of an adaptive controller with a feed forward model that can be used in a closed-loop embodiment of the present invention.

The above results indicate that open-loop control in the present invention can be quite effective in reducing cavity noise. However, as with most systems, open-loop control does not necessarily optimize a solution. This is especially true when conditions (e.g., flow conditions) are changing. Accordingly, cavity resonance reduction in the present invention can also be implemented in a closed-loop fashion as will now be explained with reference to FIGS. 5 and 6. In FIG. 5, the open-loop arrangement shown in FIG. 2 is expanded to incorporate sensor(s) and a controller. Identical reference numerals will be used for the elements that are the same as those in FIG. 2. In the closed-loop configuration, one or more sensors 50 (e.g., microphones, velocity sensors etc.) are placed in cavity 101 in order to measure cavity resonance induced by flow 14. The measured levels from sensors 50 are input to a controller 52 designed to optimize the solution (i.e., excitation of flaps 20) for a particular application with appropriate constraints on actuators. For example, the optimal solution might require the achievement of the greatest reduction in sound pressure level at the natural resonant frequency. However, in another application, the optimal solution might require the achievement of overall sound level reduction over the entire frequency spectrum.

One implementation of controller 52 is an adaptive controller shown by way of example in FIG. 6 where once again like reference numerals will be used for those elements already discussed herein. A reference signal r, i.e., the desired output signal of the system, is fed to controller 520 and reference model 522. Controller 520 determines the optimum input signal u to (amplify at amplifier 31 and) send to actuator 32. The input u is also sent to a feedforward model 524 of the cavity system. The output y of cavity 101 is compared to the predicted output $y_m$ of feedforward model 524. The error $e_m$ is used to improve feedforward model 524. Likewise, the output y is compared to the desired state output $y_r$ (closely related to r) from reference model 522. The error $e_r$ is used to update controller 520. The entire process is run in real-time and is adaptive.

The advantages of the present invention are numerous. By selectively introducing appropriate disturbances in the shear layer of a flow at the leading edge of a cavity, extreme resonant conditions can be reduced. This can be achieved at low energy expenditure by introducing the control input immediately upstream of flow separation, i.e., at the leading edge of the cavity. Control inputs can be derived from acoustic sensors located within the cavity. Cavity noise reduction can be achieved with both open and closed-loop implementations of the present invention.

Although the invention has been described relative to a specific embodiment thereof, there are numerous variations and modifications that will be readily apparent to those skilled in the art in light of the above teachings. For example, the introduction of a time-varying disturbance into the flow at the leading edge of the cavity can occur through the pure momentum injection caused by oscillating flaps (as described above), through mass/momentum injection caused by introducing a pulsed fluid jet, or by energy injection caused by the pulsed heating of the flow. It is therefore to be understood that, within the scope of the appended claims, the invention may be practiced other than as specifically described.

What is claimed as new and desired to be secured by Letters Patent of the United States is:

1. A method of reducing flow-induced resonance in a cavity comprising the steps of:

providing a structure having a cavity formed in a surface thereof, said cavity having a plurality of resonant frequencies;

causing a flow to move over said structure and past said cavity such that a leading edge and a trailing edge of said cavity are defined with respect to the direction of said flow, said flow being attached to said surface prior to said leading edge and separating from said surface at said leading edge to generate a shear layer originating at said leading edge;

providing at least one flap flush with the surface of said structure, said at least one flap having a fixed end and a free end with said fixed end being fixed relative to said structure upstream of said leading edge with respect to the direction of said flow and said free end terminating at and along said leading edge of said cavity, said at least one flap being coupled to an actuator to form a corresponding at least one active flap, and oscillating said free end of said at least one flap with respect to said structure in accordance with a time-varying function supplied to a signal generator such that energy available in said shear layer interacting with said cavity to generate resonance at at least one of said plurality of resonant frequencies is reduced.

2. A method according to claim 1, wherein said time-varying function is a periodic function.

3. A method according to claim 2 wherein said periodic function has a fundamental frequency that is different than a dominant one of said plurality of resonant frequencies of said cavity.

4. A method according to claim 1 further comprising the steps of:

monitoring resonance in said cavity caused by said shear layer; and adjusting said time-varying function based on the so-monitored resonance in said cavity.

5. A method according to claim 4 wherein said step of adjusting includes the step of adjusting the amplitude of said time-varying function.

6. A method according to claim 4 wherein said step of adjusting includes the step of adjusting the frequency of said time-varying function.

7. A method according to claim 4 wherein said step of adjusting includes the step of adjusting the phase of said time-varying function.

* * * * *